United States Patent
Briscoe

(10) Patent No.: US 10,959,739 B2
(45) Date of Patent: Mar. 30, 2021

(54) DUAL FUNCTION PIEZOELECTRIC DEVICE

(71) Applicant: Kurt Gans Briscoe, Austin, TX (US)

(72) Inventor: Kurt Gans Briscoe, Austin, TX (US)

(*) Notice: Subject to any disclaimer, the term of this patent is extended or adjusted under 35 U.S.C. 154(b) by 88 days.

(21) Appl. No.: 16/151,522

(22) Filed: Oct. 4, 2018

(65) Prior Publication Data
US 2019/0038297 A1  Feb. 7, 2019

Related U.S. Application Data

(63) Continuation of application No. PCT/US2017/025895, filed on Apr. 4, 2017.

(60) Provisional application No. 62/317,688, filed on Apr. 4, 2016.

(51) Int. Cl.
| | |
|---|---|
| *A61B 17/16* | (2006.01) |
| *A61C 3/03* | (2006.01) |
| *A61B 17/32* | (2006.01) |
| *A61C 8/00* | (2006.01) |
| *B06B 1/02* | (2006.01) |
| *A61B 17/00* | (2006.01) |

(52) U.S. Cl.
CPC .......... *A61B 17/1673* (2013.01); *A61B 17/16* (2013.01); *A61B 17/320068* (2013.01); *A61C 3/03* (2013.01); *A61C 8/0089* (2013.01); *B06B 1/0215* (2013.01); *A61B 2017/00146* (2013.01); *A61B 2017/00367* (2013.01); *A61B 2017/320082* (2017.08)

(58) Field of Classification Search
CPC ................ A61B 17/1673; A61B 17/16; A61B 17/320068; A61C 3/03; A61C 8/0089; B06B 1/0215
USPC .......................................................... 433/119
See application file for complete search history.

(56) References Cited

U.S. PATENT DOCUMENTS

| | | |
|---|---|---|
| 4,827,911 A | 5/1989 | Broadwin et al. |
| 6,695,847 B2 | 2/2004 | Bianchetti et al. |
| 6,716,030 B1 | 4/2004 | Bulard et al. |
| 7,112,063 B2 | 9/2006 | Bulard et al. |
| 8,043,089 B2 | 10/2011 | Bulard et al. |
| 8,651,866 B2 | 2/2014 | Bulard et al. |
| 8,773,001 B2 * | 7/2014 | Wiener ............. A61B 18/1445 310/323.01 |
| 8,779,648 B2 * | 7/2014 | Giordano ............ A61B 5/0538 310/317 |
| 9,107,689 B2 * | 8/2015 | Robertson .......... A61B 17/3207 |
| 9,237,921 B2 * | 1/2016 | Messerly ........... A61B 18/1442 |
| 9,427,249 B2 * | 8/2016 | Robertson ........ A61B 17/22004 |
| 2005/0037319 A1 | 2/2005 | Bulard et al. |
| 2006/0269903 A1 | 11/2006 | Bulard et al. |
| 2006/0275735 A1 | 12/2006 | Bulard et al. |
| 2007/0015102 A1 | 1/2007 | Vercellotti et al. |
| 2008/0241791 A1 | 10/2008 | Bulard et al. |
| 2010/0167235 A1 | 7/2010 | Vercellotti et al. |
| 2010/0240009 A1 | 9/2010 | Gogamoiu |
| 2011/0213397 A1 | 9/2011 | Mathonnet |
| 2012/0034578 A1 | 2/2012 | Bulard et al. |
| 2013/0045461 A1 | 2/2013 | Misch |
| 2013/0101961 A1 | 4/2013 | Bulard |
| 2014/0005704 A1 | 1/2014 | Vakharia et al. |

\* cited by examiner

*Primary Examiner* — Nicholas D Lucchesi
(74) *Attorney, Agent, or Firm* — Norris McLaughlin, P.A.

(57) ABSTRACT

A piezoelectric device comprising:
(a) a handpiece for holding by a user;
(b) a cutting insert for said handpiece;
(c) an ultrasound transducer disposed within the handpiece, the ultrasound transducer capable of providing first and second ultrasound frequency vibrations to the cutting insert in response to an electrical signal; and
(d) a switch allowing the user to control the electrical signal and thereby provide either said first or second ultrasound frequency vibrations to the cutting insert.
The device is useful in a method of placing an implant into an implant site comprising cutting overlying gingival tissue at a first ultrasound frequency capable of cutting soft tissue, then switching to a second ultrasound frequency capable of cutting the underlying jawbone.

7 Claims, No Drawings

DUAL FUNCTION PIEZOELECTRIC DEVICE

PRIORITY CLAIM

The present application is a continuation of International Patent Application No. PCT/US2017/025895, filed Apr. 4, 2017, which claims priority of U.S. Provisional Application Ser. No. 62/317,688, filed Apr. 4, 2016, the entire contents of which patent applications are incorporated herein by reference.

BACKGROUND OF THE INVENTION

1. Field of the Invention

The present invention relates to a dual function piezoelectric device.

2. Description of Related Art

Piezoelectric devices are known for use in dentistry, including the preparation of holes in jaw bone for placing dental implants. See, for example, U.S. Pat. No. 6,695,847; and U.S. Patent Publications Nos. 2007/0015102; 2010/0167235; 2010/0240009; and 2013/0045461; the entire contents of which documents are incorporated herein by reference. The use of piezoelectric devices, which vibrate rather than rotate, for such purposes has a number of advantages compared to conventional drills, including: (a) greater precision; (b) reduction of heat produced during the cutting; (c) production of holes freer of bone debris; and (d) selective drilling of bone tissues.

The latter advantage relies on the fact that the ultrasound frequencies useful to drill bone tissues (20-30 kHz) are ineffective to for soft tissues, the cutting of which requires higher frequencies (50-60 kHz). Accordingly, by setting the frequency to the range wherein bone is impacted but soft tissues are not, it is possible to impact bone selectively.

However, this selectivity comes at the cost that at the start of the implant procedure the inability of the piezoelectric devices described in these documents to impact soft tissue requires that the soft tissue covering jaw bone be reflected, i.e., cut or folded back to expose the underlying bone. See, for example, paragraph [0050] of U.S. Patent Publication No. 2007/0015102.

Reflection is traumatic of the soft tissues and there remains a need to provide a less invasive way of preparing the implant site.

SUMMARY OF THE INVENTION

The present invention relates in a first embodiment to a piezoelectric device comprising:
- (a) a handpiece for holding by a user;
- (b) a cutting insert for said handpiece;
- (c) an ultrasound transducer disposed within the handpiece, the ultrasound transducer capable of providing first and second ultrasound frequency vibrations to the cutting insert in response to an electrical signal; and
- (d) a switch allowing the user to control the electrical signal and thereby provide either said first or second ultrasound frequency vibrations to the cutting insert.

The present invention relates in a second embodiment to a method of placing a dental implant into an implant site in the jaw bone of a patient, said method comprising:
- (a) providing the inventive piezoelectric device;
- (b) switching the piezoelectric device to a first ultrasound frequency vibration capable of cutting soft tissue and using the piezoelectric device to create a first hole in gingival tissue covering underlying jaw bone at the implant site;
- (c) switching the piezoelectric device to a second ultrasound frequency vibration capable of cutting bone and using the piezoelectric device to create a second hole in the underlying jaw bone at the implant site; and
- (d) placing the implant through said first and second holes into the jaw bone.

DETAILED DESCRIPTION OF THE INVENTION

Details regarding the design and use of piezoelectric devices are well-known in the art and are not repeated here. See, again, for example, U.S. Pat. No. 6,695,847; and U.S. Patent Publications Nos. 2007/0015102; 2010/0167235; 2010/0240009; and 2013/0045461; the entire contents of which documents are incorporated herein by reference.

Dental implants, including mini-implants, are also well-known in the art and are not detailed here. See, for example, U.S. Pat. Nos. 6,716,030; 7,112,063; 8,043,089; and 8,651,866; and U.S. Patent Publications Nos. 2005/0037319; 2006/0269903; 2006/0275735; 2008/0241791; 2012/0034578; and 2013/0101961; the entire contents of which patents and applications are incorporated herein by reference.

Cutting of soft tissues, as is known in the art, generally requires higher ultrasound vibration frequencies, for example, 50-70 kHz, preferably 50-60 kHz.

Cutting of bone, on the other hand, as is also known in the art, generally requires lower ultrasound vibration frequencies, for example, 15-40 kHz, preferably 20-30 kHz.

The inventive device involves manipulating the known devices to produce ultrasound frequencies in the two different ultrasound frequency ranges, one of which will cut bone and the other of which will cut soft tissue and then configuring the device so that the respective ranges are selectable with a switch. This should easily be within the skill of the ordinary practitioner in the art.

The switch is most preferably located on the handpiece but could also be located on the console supplying electricity and hydraulics to the handpiece. Typically, such consoles have a keyboard that can be operated by the operator to control the control electronics of the handpiece. Such console can be designed to include a switch for toggling between soft tissue and bone cutting modes.

Instead of one transducer, it may be preferable in some designs to have dedicated transducers for each respective frequency range, i.e., a first transducer to be activated for the purpose of cutting gingival tissue, and a second transducer to be activated for the purpose of cutting jaw bone.

The implant can be any suitable implant, but is preferably a mini-implant, as are well-known in the art.

The hole produced in the jawbone can either be a minimal starter hole, or a full-depth osteotomy.

While the prior art hails the selectivity of bone cutting without impact on soft tissues, the invention here is based on the realization that cutting of soft tissues is advantageous at the start of the implant placement procedure and, therefore, a device that is capable of selectively cutting first soft tissue and then bone is desirable.

The present invention has the practical advantages that it avoids the need to reflect soft tissue at the start of the implant placement procedure and, therefore, also the soft tissue trauma caused thereby. The present invention also avoids the rotational trauma caused by conventional drills. The present invention also has the further practical advantage that once the gingival tissue overlying the implant site has been breached, and jawbone is encountered, the cutting will cease automatically, and the ultrasonic vibration frequency selector can be switched to a bone cutting mode and the underlying jawbone cut without any threat to nerves and other soft tissue structures in the jawbone interior. Moreover, the present invention dispenses with the need to use multiple procedures to prepare the implant site, such as reflection or drilling then ultrasound, and, thus, expedites the entire implant site preparation process.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A method of placing a dental implant into an implant site in the jawbone of a patient, said method comprising:
    (a) providing a piezoelectric device comprising:
        (i) a handpiece for holding by a user;
        (ii) a cutting insert for said handpiece;
        (iii) an ultrasound transducer disposed within the handpiece, the ultrasound transducer configured to provide first and second ultrasound frequency vibrations to the cutting insert in response to an electrical signal, wherein the first ultrasound frequency vibration cuts soft tissue, and wherein the second ultrasound frequency vibration cuts bone; and
        (iv) a switch allowing the user to control the electrical signal so that the user by manipulating the switch selects to provide either said first or second ultrasound frequency vibrations to the cutting insert;
    (b) switching the piezoelectric device to said first ultrasound frequency vibration and using the piezoelectric device to create a first hole in gingival tissue covering underlying jawbone at the implant site;
    (c) switching the piezoelectric device to said second ultrasound frequency vibration and using the piezoelectric device to create a second hole in the underlying jawbone at the implant site; and
    (d) placing the implant through said first and second holes into the jawbone.

2. The method according to claim 1, wherein the implant is a mini-implant.

3. The method according to claim 1, wherein the first ultrasound frequency vibration is 50-60 kHz.

4. The method according to claim 1, wherein the second ultrasound frequency vibration is 20-30 kHz.

5. The method according to claim 1, wherein the switch is a toggle switch.

6. A method of placing a dental implant into an implant site in the jawbone of a patient, said method comprising:
    (a) providing a piezoelectric device comprising:
        (i) a handpiece for holding by a user;
        (ii) at least one cutting insert for said handpiece;
        (iii) an ultrasound transducer disposed within the handpiece, the ultrasound transducer configured to provide first and second ultrasound frequency vibrations to the cutting insert in response to an electrical signal, the first ultrasound frequency vibration being 50-60 kHz, and the second ultrasound frequency vibration being 20-30 kHz; and
        (iv) a switch on the handpiece allowing the user to control the electrical signal so that the user by manipulating the switch selects to provide either said first or second ultrasound frequency vibrations to the cutting insert;
    (b) switching the piezoelectric device to said first ultrasound frequency vibration and using the piezoelectric device to create a first hole in gingival tissue covering underlying jawbone at the implant site;
    (c) switching the piezoelectric device to said second ultrasound frequency vibration and using the piezoelectric device to create a second hole in the underlying jawbone at the implant site; and
    (d) placing the implant through said first and second holes into the jawbone.

7. The method according to claim 6, wherein the switch is a toggle switch.

* * * * *